(12) United States Patent
Griswold et al.

(10) Patent No.: US 11,179,052 B2
(45) Date of Patent: Nov. 23, 2021

(54) DISTINGUISHING DISEASED TISSUE FROM HEALTHY TISSUE BASED ON TISSUE COMPONENT FRACTIONS USING MAGNETIC RESONANCE FINGERPRINTING (MRF)

(71) Applicant: Case Western Reserve University, Cleveland, OH (US)

(72) Inventors: Mark A. Griswold, Shaker Heights, OH (US); Anagha Deshmane, Cleveland Heights, OH (US); Jeffrey Sunshine, Pepper Pike, OH (US)

(73) Assignee: Case Western Reserve University, Cleveland, OH (US)

( * ) Notice: Subject to any disclaimer, the term of this patent is extended or adjusted under 35 U.S.C. 154(b) by 337 days.

(21) Appl. No.: 16/159,888

(22) Filed: Oct. 15, 2018

(65) Prior Publication Data

US 2019/0046052 A1 Feb. 14, 2019

Related U.S. Application Data

(62) Division of application No. 14/682,142, filed on Apr. 9, 2015, now Pat. No. 10,143,389.

(Continued)

(51) Int. Cl.
*A61B 5/026* (2006.01)
*A61B 5/055* (2006.01)
(Continued)

(52) U.S. Cl.
CPC ............ *A61B 5/0263* (2013.01); *A61B 5/055* (2013.01); *A61B 5/4064* (2013.01);
(Continued)

(58) Field of Classification Search
CPC ........ G01R 1/00; G01N 1/00; G01N 2201/00; G01T 1/00; G06K 1/00; A61B 1/00; A61B 2218/00; A61N 1/00
See application file for complete search history.

(56) References Cited

U.S. PATENT DOCUMENTS 8,723,518 B2 5/2014 Seiberlich
9,097,781 B2 8/2015 Griswold
(Continued)

FOREIGN PATENT DOCUMENTS

| | | |
|---|---|---|
| CN | 103654779 | 3/2016 |
| DE | 102014223388 | 5/2016 |
| WO | 2018065618 | 4/2018 |

OTHER PUBLICATIONS

Garner, B.A., A Dictionary of Modern Legal Usage 624 (2d. Ed. 1995).

(Continued)

*Primary Examiner* — Jermele M Hollington
*Assistant Examiner* — Temilade S Rhodes-Vivour
(74) *Attorney, Agent, or Firm* — Quarles & Brady LLP

(57) ABSTRACT

Example embodiments associated with characterizing a sample using NMR fingerprinting are described. One example NMR apparatus includes an NMR logic that repetitively and variably samples a (k, t, E) space associated with an object to acquire a set of NMR signals that are associated with different points in the (k, t, E) space. Sampling is performed with t and/or E varying in a non-constant way. The NMR apparatus may also include a signal logic that produces an NMR signal evolution from the NMR signals and a characterization logic that characterizes a tissue in the object as a result of comparing acquired signals to reference signals. Example embodiments facilitate distinguishing dis- (Continued)

eased tissue from healthy tissue based on tissue component fractions identified using the NMR fingerprinting.

19 Claims, 10 Drawing Sheets

Related U.S. Application Data

(60) Provisional application No. 61/982,588, filed on Apr. 22, 2014.

(51) Int. Cl.
| | | |
|---|---|---|
| A61B 5/00 | (2006.01) | |
| G01R 33/563 | (2006.01) | |
| G01R 33/44 | (2006.01) | |
| G01R 33/48 | (2006.01) | |
| G01R 33/565 | (2006.01) | |
| G01R 33/56 | (2006.01) | |
| G01R 33/561 | (2006.01) | |
| A61B 1/00 | (2006.01) | |
| G01R 1/00 | (2006.01) | |
| A61B 17/00 | (2006.01) | |
| G06T 1/00 | (2006.01) | |
| G01R 33/50 | (2006.01) | |

(52) U.S. Cl.
CPC ....... *G01R 33/448* (2013.01); *G01R 33/4818* (2013.01); *G01R 33/5602* (2013.01); *G01R 33/5608* (2013.01); *G01R 33/5611* (2013.01); *G01R 33/56366* (2013.01); *G01R 33/56563* (2013.01); *A61B 1/00* (2013.01); *A61B 5/742* (2013.01); *A61B 17/00* (2013.01); *A61B 2217/00* (2013.01); *A61B 2218/00* (2013.01); *G01R 1/00* (2013.01); *G01R 33/4828* (2013.01); *G01R 33/50* (2013.01); *G06T 1/00* (2013.01); *G06T 2200/00* (2013.01)

(56) References Cited

U.S. PATENT DOCUMENTS

| 9,568,579 | B2 | 2/2017 | Jerecic | |
|---|---|---|---|---|
| 9,757,047 | B2 | 9/2017 | Chappell | |
| 9,851,425 | B2 | 12/2017 | Lee | |
| 9,869,739 | B2 | 1/2018 | Griswold | |
| 10,136,824 | B2 | 11/2018 | Hernandez-Garcia | |
| 2004/0142496 | A1* | 7/2004 | Nicholson | G01R 33/4625 436/536 |
| 2004/0214348 | A1* | 10/2004 | Nicholson | G01R 33/4625 436/518 |
| 2006/0244447 | A1 | 11/2006 | Michaeli | |
| 2009/0142273 | A1 | 6/2009 | Pagel | |
| 2010/0261993 | A1 | 10/2010 | van der Kouwe | |
| 2011/0199084 | A1 | 8/2011 | Hasan | |
| 2012/0235678 | A1* | 9/2012 | Seiberlich | G01R 33/543 324/307 |
| 2012/0262165 | A1 | 10/2012 | Griswold | |
| 2012/0262166 | A1 | 10/2012 | Griswold | |
| 2012/0274323 | A1* | 11/2012 | He | G01R 33/5607 324/309 |
| 2012/0280686 | A1 | 11/2012 | White | |
| 2013/0265047 | A1* | 10/2013 | Griswold | G01R 33/56 324/309 |
| 2013/0271132 | A1* | 10/2013 | Griswold | G01R 33/56 324/309 |
| 2014/0084922 | A1 | 3/2014 | Fu | |
| 2014/0167754 | A1 | 6/2014 | Jerecic | |
| 2014/0232399 | A1 | 8/2014 | Griswold | |
| 2014/0266199 | A1 | 9/2014 | Griswold | |
| 2014/0292330 | A1 | 10/2014 | Gulani | |
| 2015/0301138 | A1 | 10/2015 | Griswold | |
| 2015/0301140 | A1 | 10/2015 | Lee | |
| 2015/0301144 | A1 | 10/2015 | Griswold | |
| 2015/0301147 | A1 | 10/2015 | Gulani | |
| 2015/0302579 | A1* | 10/2015 | Griswold | G01R 33/5608 382/128 |
| 2015/0316634 | A1 | 11/2015 | Griswold | |
| 2016/0282430 | A1 | 9/2016 | Gulani | |
| 2017/0016971 | A1 | 1/2017 | Heisman | |
| 2017/0146623 | A1 | 5/2017 | Cohen | |

OTHER PUBLICATIONS

Heid, O., M. Deimling, and W. Huk. "QUEST—a quick echo split nmr imaging technique." Magnetic resonance in medicine 29.2 (1993): 280-283.

Lee, G. R., et al. (2013) Rapid time-resolved magnetic resonance angiography via a multiecho radial trajectory and GraDes reconstruction, Magnetic Resonance in Medicine, 69(2): 346-59.

Ma et al., Magnetic Resonance Fingerprinting, Nature 495, 187-192 (Mar. 14, 2013).

Wright, K. L., et al. "Estimation of perfusion properties with MR fingerprinting arterial spin labeling." Magnetic resonance imaging 50 (2018): 68-77.

Wright, K. L., et al. "Theoretical framework for MR fingerprinting with ASL: simultaneous quantification of CBF, transit time, and T1." Proc Int Soc Magn Reson Med. vol. 22. 2014.

\* cited by examiner

US 11,179,052 B2

DISTINGUISHING DISEASED TISSUE FROM HEALTHY TISSUE BASED ON TISSUE COMPONENT FRACTIONS USING MAGNETIC RESONANCE FINGERPRINTING (MRF)

CROSS REFERENCE TO RELATED APPLICATIONS

This application is a divisional of U.S. patent application Ser. No. 14/682,142, filed Apr. 9, 2015, which claims benefit of U.S. Provisional Patent Application 61/982,588, filed Apr. 22, 2014, both of which are incorporated herein by reference in their entirety.

STATEMENT REGARDING FEDERALLY SPONSORED RESEARCH

This invention was made with government support under EB017219 awarded by the National Institutes of Health. The government has certain rights in the invention.

BACKGROUND

Characterizing resonant species using nuclear magnetic resonance (NMR) can include identifying different properties of a resonant species (e.g., T1 spin-lattice relaxation, T2 spin-spin relaxation, proton density). Other properties like tissue types and super-position of attributes can also be identified using NMR signals. These properties and others may be identified simultaneously using magnetic resonance fingerprinting (MRF), which is described in *Magnetic Resonance Fingerprinting*, Ma D et al., Nature 2013:495, (7440): 187-192.

Conventional magnetic resonance (MR) pulse sequences include repetitive similar preparation phases, waiting phases, and acquisition phases that serially produce signals from which images can be made. The preparation phase determines when a signal can be acquired and determines the properties of the acquired signal. For example, a first pulse sequence may produce a T1-weighted signal at a first echo time (TE) while a second pulse sequence may produce a T2-weighted signal at a second TE. These conventional pulse sequences typically provide qualitative results where data are acquired with various weightings or contrasts that highlight a particular parameter (e.g., T1 relaxation, T2 relaxation).

When MR images are generated, they may be viewed by a radiologist and/or surgeon who interprets the qualitative images for specific disease signatures. The radiologist may examine multiple image types (e.g., T1-weighted, T2-weighted) acquired in multiple imaging planes to make a diagnosis. The radiologist or other individual examining the qualitative images may need particular skill to be able to assess changes from session to session, from machine to machine, and from machine configuration to machine configuration.

Unlike conventional MRI, MRF employs a series of varied sequence blocks that simultaneously produce different signal evolutions in different resonant species (e.g., tissues) to which the RF is applied. The term "resonant species", as used herein, refers to an item (e.g., water, fat, tissue, material) that can be made to resonate using NMR. By way of illustration, when RF energy is applied to a volume that has bone and muscle tissue, then both the bone and muscle tissue will produce an NMR signal. However the "bone signal" and the "muscle signal" will be different and can be distinguished using MRF. The different signals can be collected over a period of time to identify a signal evolution for the volume. Resonant species in the volume can then be characterized by comparing the signal evolution to known evolutions. Characterizing the resonant species may include identifying a material or tissue type, or may include identifying MR parameters associated with the resonant species. The "known" evolutions may be, for example, simulated evolutions or previously acquired evolutions. A large set of known evolutions may be stored in a dictionary.

BRIEF DESCRIPTION OF THE DRAWINGS

The accompanying drawings, which are incorporated in and constitute a part of the specification, illustrate various example systems, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
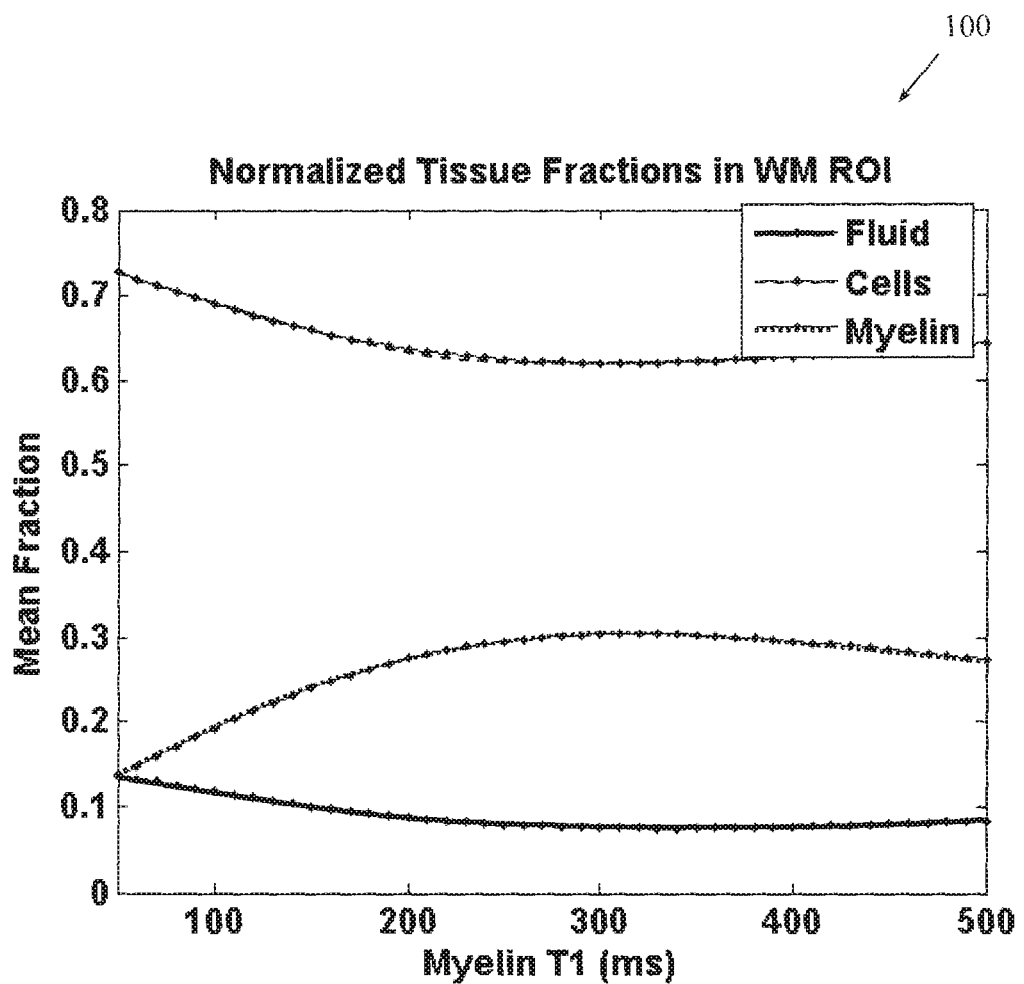
FIG. 1 illustrates data associated with normal white matter in a healthy volunteer.

Magnetic Resonance Fingerprinting (MRF) causes resonant species in an object to produce pseudorandom MR signal evolutions. The pseudorandom signal evolutions may be compared to a dictionary of stored signal evolutions. The stored signal evolutions may be from previous acquisitions or may even be from theoretical models. For example, the stored signal evolutions can be from a set described by:

$$SE = \sum_{i=1}^{N_S} \prod_{i=1}^{N_A} \sum_{j=1}^{N_{RF}} R_{i(\alpha)} R_{RF_{ij}(\alpha,\phi)} R(G) E_i(T1, T2, \ldots) DPdM_0$$

-continued or $$SE = \sum_{i=1}^{N_S} \prod_{i=1}^{N_A} \prod_{j=1}^{N_{RF}} R_i(\alpha) R_{RF_{ij}(\alpha,\phi)} R(G) E_i(T1, T2, \ldots) DPdM_0$$

where:

SE is a signal evolution, $N_S$ is a number of spins, $N_A$ is a number of sequence blocks, $N_{RF}$ is a number of RF pulses in a sequence block, $\alpha$ is a flip angle, $\phi$ is a phase angle, $Ri(\alpha)$ is a rotation due to off resonance, $R_{RFij}(\alpha, \phi)$ is a rotation due to RF differences, $R(G)$ is a rotation due to a gradient, T1 is spin-lattice relaxation, T2 is spin-spin relaxation, D is diffusion relaxation, Pd is proton density, $E_i(T1, T2, \ldots)$ is decay due to relaxation differences, and $M_0$ is the default or equilibrium magnetization.

Some MRF investigations may involve a sample for which there is a priori knowledge about the resonant species that are likely to be encountered. The a priori knowledge may even include information concerning possible or expected ratios of the amounts of the resonant species to be encountered in the sample. When the sample has some properties (e.g., T relaxation time, T2 relaxation time) that are likely to fall in a certain range, then it may be possible to simplify or even focus the pattern matching portion of MRF.

For example, in a human brain there is typically a finite set of materials that are arranged in a finite set of configurations and ratios. Said another way, human brains are remarkably similar. Thus, although MRF can match signals against a theoretically enormous dictionary of stored signal evolutions, more sophisticated and focused pattern matching may be possible using a dictionary that includes "brain specific" or even "brain disease specific" signal evolutions. This focused pattern matching may facilitate quantitative magnetic resonance based diagnosis of, for example, Multiple Sclerosis (MS).

In one embodiment, an MRF dictionary could be populated with signal evolutions that are associated with fluids found in the brain. A received signal evolution could then be compared to signal evolutions in the MRF dictionary to determine whether the area from which the signal evolution was received was fluid. Similarly, the MRF dictionary could be populated with signal evolutions that are associated with cells found in the brain. A received signal evolution could then be compared to signal evolutions in the dictionary to determine whether the area from which the signal evolution was received was cells.

The dictionary may be able to store multiple types of signal evolutions. For example, the dictionary could store signal evolutions that are associated with both fluids and cells. Thus, a received signal evolution could be compared to signal evolutions in the dictionary to determine whether the area from which the signal evolution was received contained water, cells, or a combination thereof.

If signal evolutions stored in the dictionary are constrained in certain ways, which is feasible when the object being subjected to MRF has well known properties, then a signal evolution may be modeled in a way that makes the signal evolution well-suited for an inverse operation that may provide additional information when compared to conventional systems. For example, the additional information may facilitate determining the amount of different components present in the sample that contributed to the received signal.

In one embodiment, signal evolutions stored in the MRF dictionary may be constrained to model signals from a small number (e.g., 2, 3, 4) of components (e.g., fluids, cells, myelin water) expected to be in the sample. The signal evolutions may also be constrained by fixing some MR parameters (e.g., T1, T2) for some components while letting other MR parameters vary for other components. The signal evolution may then be modelled using a forward operation (e.g., weighted sum of dictionary entries) applied to known components. A received signal evolution can then be analyzed using, for example, an inverse operation (e.g., matrix pseudo-inverse) to identify the relative fractions of the components (e.g., fluids, cells) in the sample that contributed to the received signal evolution. While an inverse operation is described, more generally information about a combination of resonant species that contribute to a signal evolution may be retrievable for the signal evolution.

While fluids in the brain and cells in the brain are described, additional components may be included. For example, to study MS, signal evolutions associated with myelin water may be included with the signal evolutions for fluids and cells. In this example, a signal evolution may be modelled using a weighted sum of dictionary entries corresponding to fluids, cells, and myelin water. In this example, a matrix pseudo-inverse may be applied to a matched received signal evolution to identify the percentage of fluids, cells, and myelin water in a sample. If the relative fractions of fluids, cells, and myelin water are known, then diseased tissue can be distinguished from healthy tissue. In one embodiment, it may be possible to distinguish normal white matter from normal appearing but actually abnormal white matter in an MS patient. Similarly, it may be possible to distinguish normal appearing but actually abnormal grey matter in an MS patient from an MS lesion. Other comparisons and distinctions between normal and diseased tissue may be possible. In one embodiment, healthy tissue may be distinguished from diseased tissue using a quantitative MR based analysis, which may improve over conventional subjective visual analysis.

The model for the signal evolutions for the known components (e.g., fluids, cells, myelin water) may be crafted to facilitate a forward operation (e.g., weighted sum) and an inverse operation (e.g., matrix pseudo-inverse). The forward operation may be used to model signal evolutions and the inverse operation may be used to determine relative fractions of components that contributed to a received signal evolution that matched to a dictionary entry. The relative fractions may then be used to distinguish healthy tissue from diseased tissue. In different embodiments, the relative fractions may be retrieved in other ways. For example, the relative fractions for resonant species components associated with a stored signal evolution may be stored in a table, in a database, or in another data structure. The matching signal evolution may be used, for example, as a key to retrieve the relative fraction information.

Figure 5:
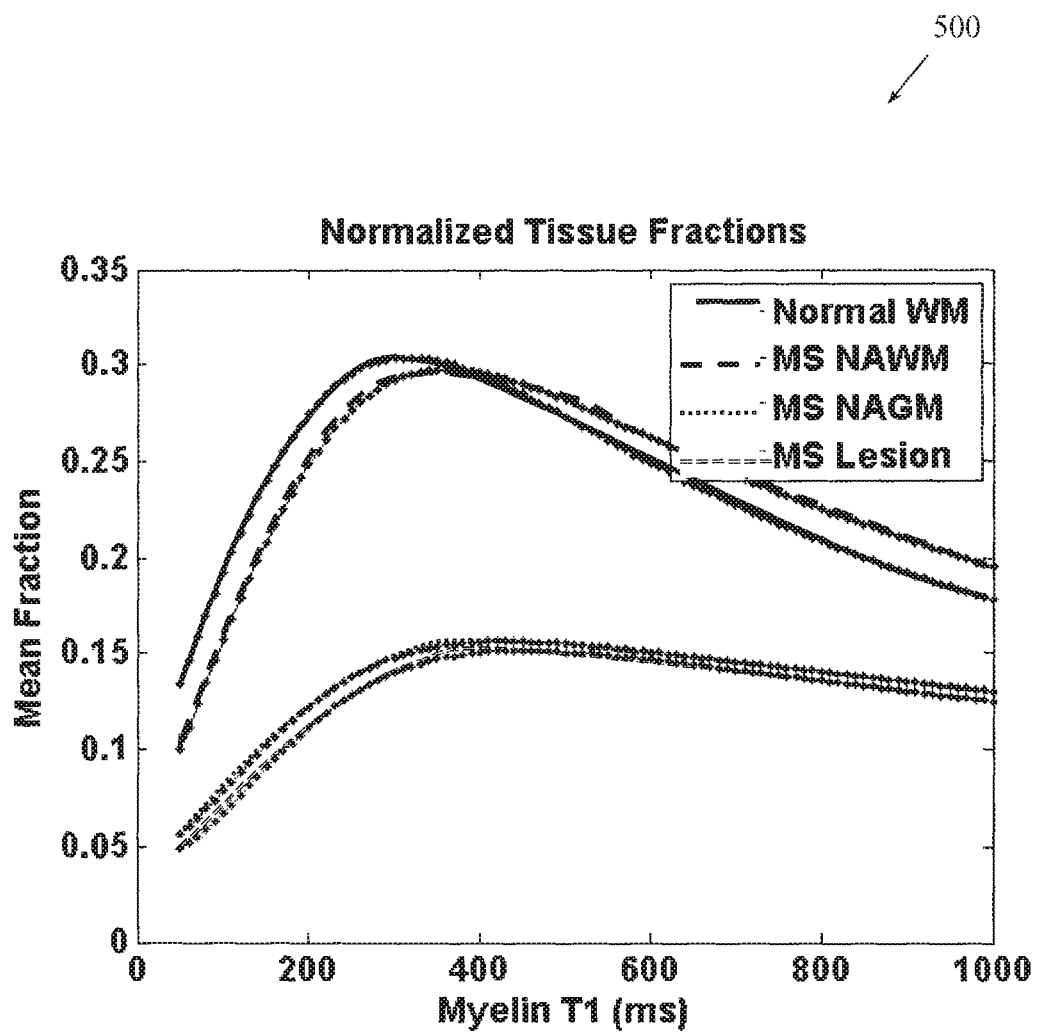
FIG. 5 illustrates a plot of one component fraction as a function of T1.

In one embodiment relevant to MS, distinguishing the tissues may include plotting myelin water as a function of T1 (see, e.g., FIG. 5). In one embodiment, one or more parameters (e.g., T1, T2) associated with a set of modeled MRF signal evolutions for a component may be varied while one or more other parameters (e.g., T1, T2) associated with the set of modeled MRF signal evolutions for the component may be held constant. For example, T1 and T2 may be held constant for a first component (e.g., fluids), T1 and T2 may be held constant for a second component (e.g., cells) and T2 may be held constant for a third component (e.g., myelin water) while T1 is varied over an interesting range (e.g., 100

µs to 5000 ms). In this example, for each value of T1 in the third component, the relative fraction of the three components may be evaluated. In one embodiment, being "held constant" may include allowing the value for the MR parameter to vary in a narrow range (e.g., within 5% of a center value).

MRF involves measuring pseudorandom MR signal evolutions produced in response to MRF pulse sequences. MRF also includes generating modeled signal evolutions that may be stored in a dictionary. The dictionary entries may be a function of several parameters. If the composition of the sample to be interrogated is known ahead of time, then a mathematical operation (e.g., weighted sum) of dictionary entries corresponding to the known components may be used to model signal evolutions and an inverse mathematical operation (e.g., matrix pseudo-inverse) may be used to compute the relative fraction of components assumed to be present based on a received signal evolution.

Experiments using example apparatus and methods were performed using MRF data from the brains of healthy volunteers and patients with multiple sclerosis. Four regions of interest were defined: normal white matter from the healthy volunteer, normal appearing white matter from an MS patient, normal appearing grey matter from an MS patient, and a demyelinated lesion from the MS patient. Three modeled components were included in the dictionary. In one embodiment, the three modeled components were fluid found in a human brain, cells found in a human brain, and myelin water. In generating the components, the T1 and T2 parameters were held constant in two of the components, while in the third component the T2 parameter was held constant and the T1 parameter was varied from 100 µs to 5000 ms. Different combinations of holding parameters constant and varying parameters may be employed. For the values of T1 in the third component, the relative fractions of the three components were calculated. Plotting the third component fraction as a function of T1 revealed discernable differences in the composition of the normal white matter from a healthy volunteer compared to normal appearing white matter in an MS patient, normal appearing grey matter in the MS patient, and the MS lesion.

Figure 2:
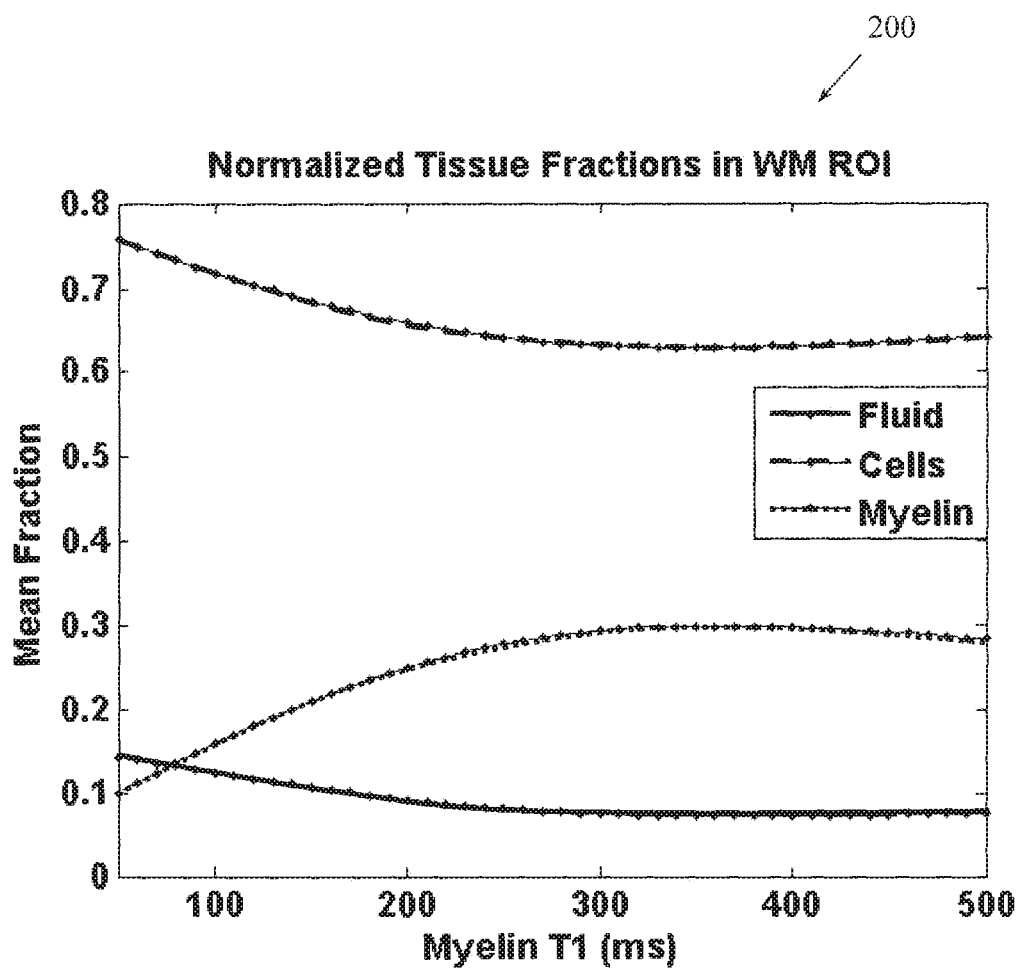
FIG. 2 illustrates data associated with normal appearing white matter in an MS patient.
Figure 3:
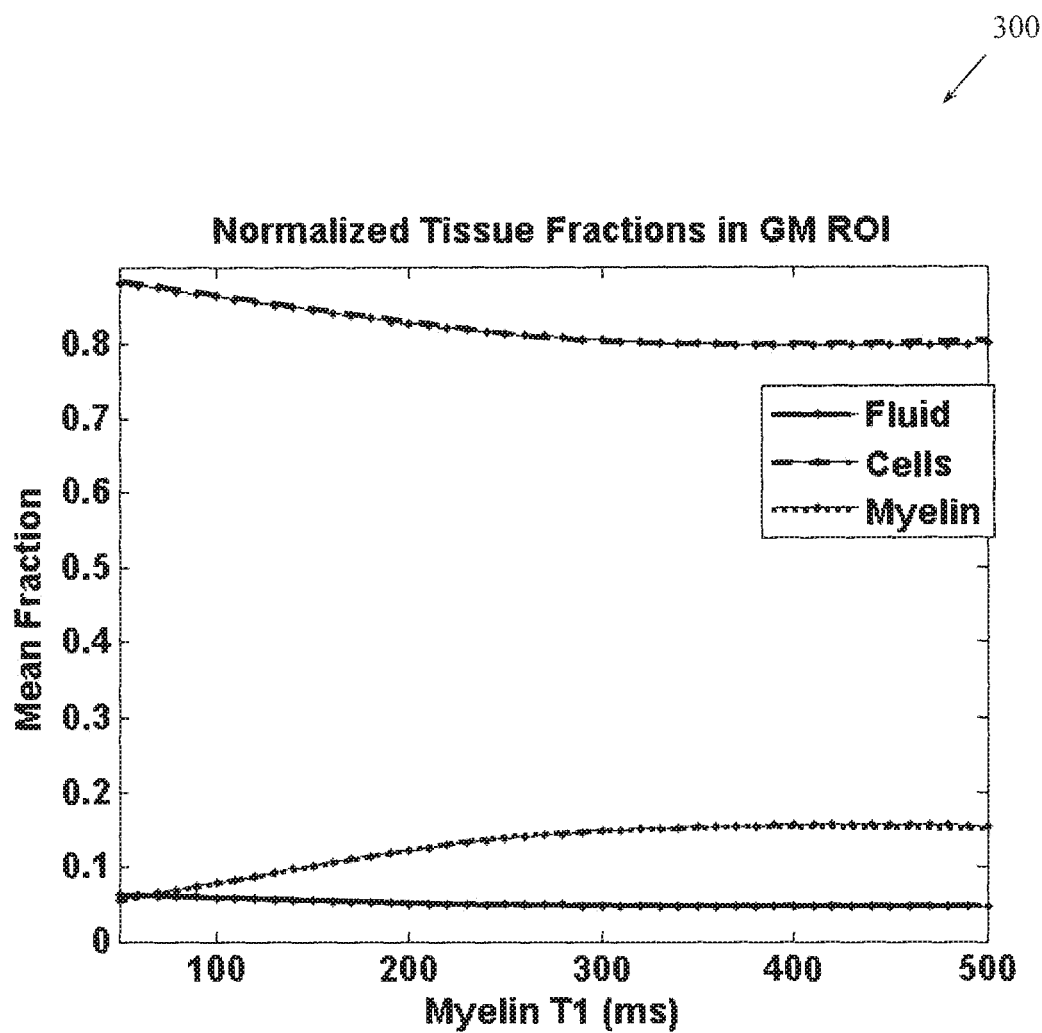
FIG. 3 illustrates data associated with normal appearing grey matter in an MS patient.
Figure 4:
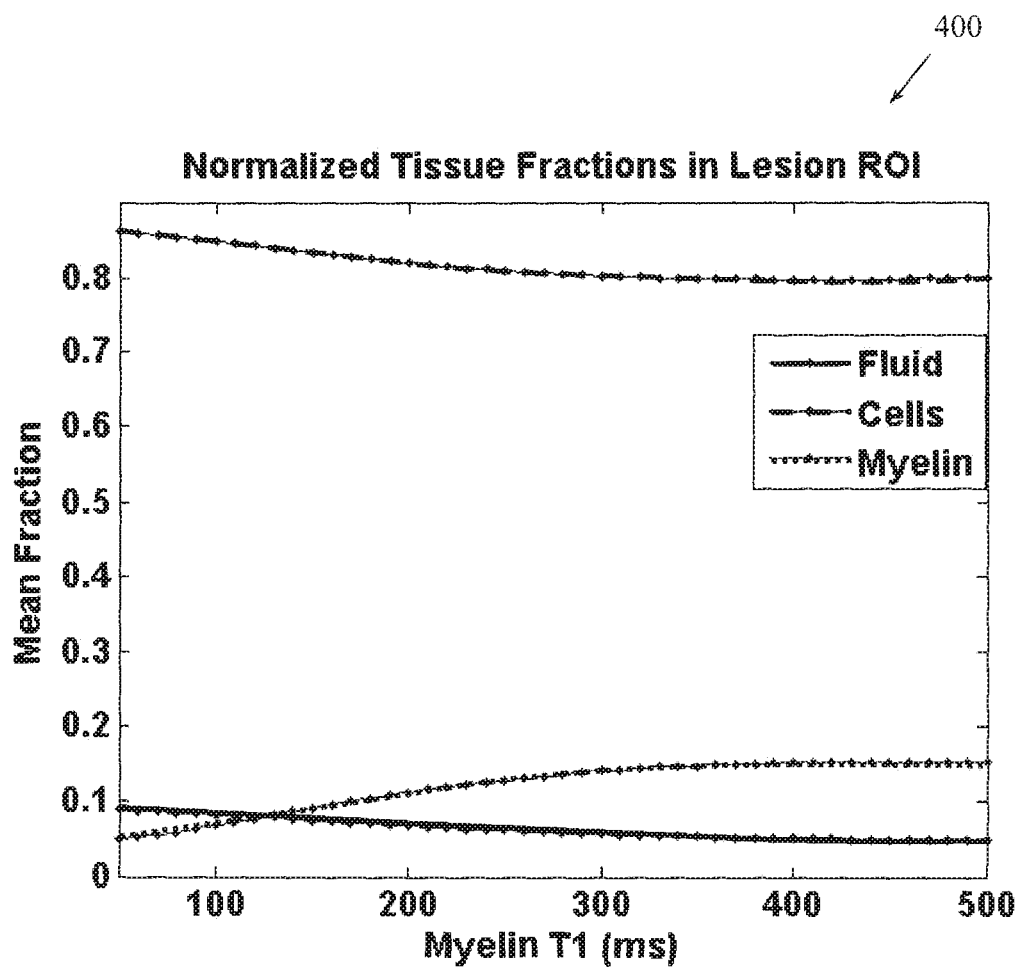
FIG. 4 illustrates data associated with a demyelinated lesion in the MS patient.

The results of the experiments are presented in FIGS. 1-5. FIG. 1 illustrates a graph 100 of relative fractions of fluid, cells, and myelin water for normal white matter using different values for T1 for myelin water. FIG. 2 illustrates a graph 200 of relative fractions of fluid, cells, and myelin water for normal appearing white matter in an MS patient. The relative fractions are displayed for different values of T1 for myelin water. FIG. 3 illustrates a graph 300 of relative fractions of fluid, cells, and myelin water for normal appearing grey matter in an MS patient. The relative fractions are displayed for different values of T1 for myelin water. FIG. 4 illustrates a graph 400 of relative fractions of fluid, cells, and myelin water for an MS lesion in an MS patient. The relative fractions are displayed for different values of T1 for myelin water. Graphs 100, 200, 300, and 400 are easily distinguishable, proving the correctness of MRF based identification of relative fractions of resonant species associated with MS.

FIG. 5 illustrates a graph 500 of myelin water fractions for normal white matter, MS normal appearing white matter, MS normal appearing grey matter, and an MS lesion. The myelin water fractions for each category are clearly different.

MRF simultaneously provides quantitative data concerning multiple MR parameters. Observed signal evolutions are matched to dictionary entries using, for example, template matching or other matching or comparing processes. In one example matching process, the inner product is computed between a noisy acquired signal and entries in a dictionary to find the stored signal evolution to which an acquired signal evolution most closely matches. In other examples, other pattern matching or similarity finding approaches are performed. Values related to the dictionary entry that matched the acquired noisy signal may then be retrieved. In one example, the values may be stored in the dictionary, while in another example MR parameters may be stored in a data store separate from the dictionary. In one embodiment, the values may be retrieved by performing a mathematical operation on a signal evolution.

The following includes definitions of selected terms employed herein. The definitions include various examples and/or forms of components that fall within the scope of a term and that may be used for implementation. The examples are not intended to be limiting. Both singular and plural forms of terms may be within the definitions.

References to "one embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage medium", as used herein, refers to a non-transitory medium that stores signals, instructions and/or data. A computer-readable medium may take forms, including, but not limited to, non-volatile media, and volatile media. Non-volatile media may include, for example, optical disks, magnetic disks, and so on. Volatile media may include, for example, semiconductor memories, dynamic memory, and so on. Common forms of a computer-readable medium may include, but are not limited to, a floppy disk, a flexible disk, a hard disk, a magnetic tape, other magnetic medium, an ASIC, a CD, other optical medium, a RAM, a ROM, a memory chip or card, a memory stick, and other media from which a computer, a processor or other electronic device can read.

"Logic", as used herein, includes but is not limited to hardware, firmware, software in execution on a machine, and/or combinations of each to perform a function(s) or an action(s), and/or to cause a function or action from another logic, method, and/or system. Logic may include a software controlled microprocessor, a discrete logic (e.g., ASIC), an analog circuit, a digital circuit, a programmed logic device, a memory device containing instructions, and so on. Logic may include one or more gates, combinations of gates, or other circuit components. Where multiple logical logics are described, it may be possible to incorporate the multiple logical logics into one physical logic. Similarly, where a single logical logic is described, it may be possible to distribute that single logical logic between multiple physical logics.

An "operable connection", or a connection by which entities are "operably connected", is one in which signals, physical communications, and/or logical communications may be sent and/or received. An operable connection may include a physical interface, an electrical interface, and/or a data interface. An operable connection may include differing combinations of interfaces and/or connections sufficient to allow operable control. For example, two entities can be operably connected to communicate signals to each other directly or through one or more intermediate entities (e.g., processor, operating system, logic, software). Logical and/or physical communication channels can be used to create an operable connection.

"User", as used herein, includes but is not limited to one or more persons, software, computers or other devices, or combinations of these.

Figure 6:
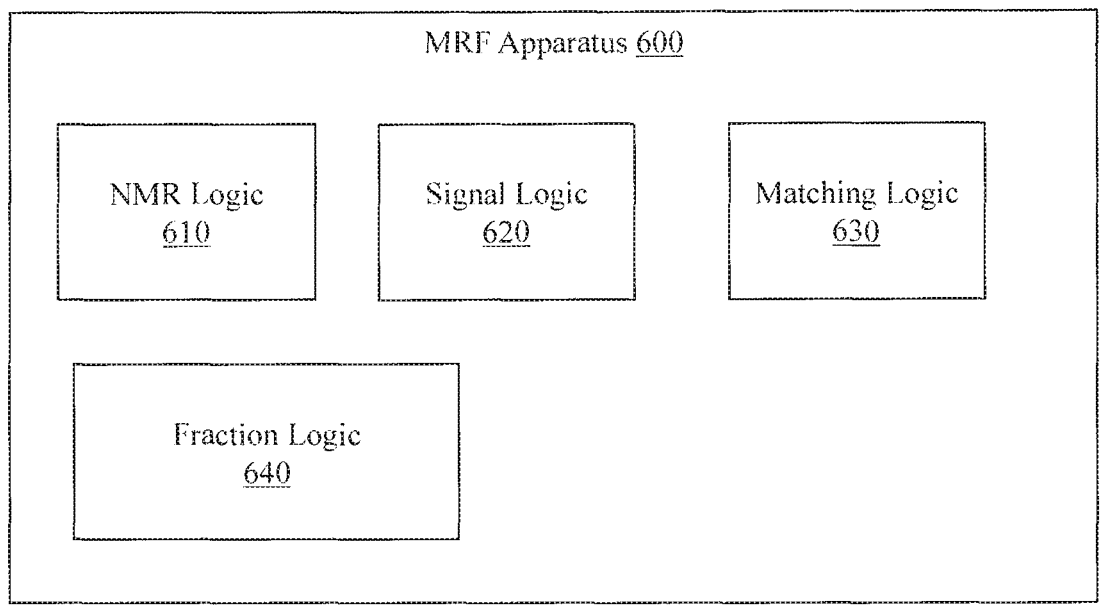
FIG. 6 illustrates an example MR apparatus associated with distinguishing healthy tissue from diseased tissue based on tissue component fractions identified using magnetic resonance fingerprinting (MRF).

FIG. 6 illustrates an MRF apparatus 600. MRF apparatus 600 may simultaneously quantify MR parameters including T1 and T2 for an object to which an MRF pulse sequence is applied. MRF apparatus 600 includes an NMR logic 610. In one embodiment, the NMR logic 610 applies RF energy to the object according to an MRF pulse sequence. NMR logic 610 repetitively and variably samples an object in a (k, t, E) space to acquire a first set of data. The first set of data may be a set of NMR signals that may have non-constant amplitude and/or phase. Members of the set of NMR signals are associated with different points in the (k, t, E) space. In different embodiments the different points are sampled according to a plan where t and/or E varies non-linearly and/or in a non-constant manner. The first set of data may have contributions of NMR signals from different resonant species in the sample that produced the first set of data. Apparatus 600 facilitates identifying the ratios of the different resonant species in the sample.

MRF apparatus 600 also includes a signal logic 620. Signal logic 620 produces an NMR signal evolution from the acquired NMR signals. The signal evolution may include a number of NMR signals acquired over a period of time. The signal evolution may have contributions from the different resonant species. Different amounts of resonant species in a sample may cause different signal evolutions to be produced. For example, a first sample that is 70% water and 30% fat may produce a first signal evolution while a second sample that is 30% water and 70% fat may produce a second, different signal evolution even though the same two resonant species are present in the samples.

MRF apparatus 600 also includes a matching logic 630. Matching logic 630 compares the produced NMR signal evolution or information associated with the produced NMR signal evolution to a collection (e.g., dictionary, database) of stored signal evolutions to find a match for the acquired NMR signal evolution. In one embodiment, information concerning relative proportions of resonant species that contributed to the selected stored signal evolution is retrievable using the match.

"Match" as used herein refers to the result of comparing signals. "Match" does not refer to an exact match, which may or may not be found. A match may be the signal that most closely resembles another signal. A match may be the first signal that matches another signal to within a threshold. A match may be found by template matching, pattern matching, model fitting, or other comparison approaches. The reference information may be, for example, a previously acquired signal evolution, a simulated signal evolution, an item derived from a signal evolution other than the produced NMR signal evolution, and other information. The reference information may include signal evolutions from different tissue types (e.g., healthy, diseased, advanced disease). The reference information may include signal evolutions that are formed from combinations of resonant species with combinations of MR parameters.

In one embodiment, the collection of stored signal evolutions includes a signal evolution having information associated with a first resonant species and a second resonant species. The information associated with the first resonant species may be produced by controlling an MR property or properties associated with the first resonant species to be constant or to be within a first known range or ranges. Information associated with the second resonant species may also be produced by controlling an MR property or properties associated with the second resonant species to be constant or to be within a second known range or ranges. When the collection of stored signal evolutions includes signal evolutions associated with a finite, small (e.g., 2, 3) number of resonant species, and when the signals used to produce the signal evolutions are constrained within well-defined ranges, then relative fractions of the resonant species that contributed to the acquired NMR signal evolution may be determined from the matched signal evolution. The relative fractions may be determined in different ways. In one example, the relative fractions may be decoded from the matched signal evolution.

In one embodiment, the first resonant species is fluid found in a human brain, the MR property for the fluid is T1, and the first known range is between 4500 ms and 5000 ms. In this embodiment, the second resonant species is myelin water found in a human brain, the MR property for the myelin water is T1, and the second known range is between 50 ms and 1000 ms. In one embodiment, the information associated with the fluid is produced by controlling T2 associated with the fluid to be within 5 ms and 1000 ms and the information associated with the myelin water is produced by controlling T2 associated with the myelin water to be within 100 μs and 1000 ms. Different ranges or constant values for T1 or T2 may be employed in different examples.

In one embodiment, the first resonant species is water interacting with cellular membranes found in a human brain, the MR property for the water interacting with cellular membranes is T1, and the first known range is between 100 μs and 5000 ms. In this embodiment, the second resonant species is myelin water found in a human brain, the MR property for the myelin water is T1, and the second known range is between 100 μs and 5000 ms. In this embodiment, the information associated with the water interacting with cellular membranes is produced by controlling T2 associated with the water interacting with cellular membranes to be within 5 ms and 1000 ms and the information associated with the myelin water is produced by controlling T2 associated with the myelin water to be within 100 μs and 1000 ms. Different ranges or constant values for T1 or T2 may be employed in different examples.

In one embodiment, more than two resonant species or components may be considered. For example, the collection of stored signal evolutions may include a signal evolution having information associated with fluid found in a human brain, cells found in a human brain, water interacting with cellular membranes, and myelin water found in a human brain. In this embodiment, the information associated with the fluid is produced by controlling T1 associated with the fluid to be between 4500 ms and 5000 ms and by controlling T2 associated with the fluid to be between 450 ms and 500 ms. In this embodiment, the information associated with the water interacting with cellular membranes is produced by controlling T1 associated with the cells to be between 1000 ms and 1500 ms and by controlling T2 associated with the fluid to be between 100 ms and 150 ms. In this embodiment, the information associated with the myelin water is produced by controlling T1 associated with the myelin water to be between 50 ms and 1000 ms and by controlling T2 associated with the fluid to be between 15 ms and 25 ms. Different ranges or constant values for T1 or T2 may be employed in different examples.

In one embodiment, the information concerning the first resonant species may be combined with the information concerning the second resonant species using a weighted sum operation. When the weighted sum approach is employed, then information concerning relative proportions of resonant species that contributed to the selected stored signal evolution may be retrievable from the selected stored signal evolution in response to performing a matrix pseudo-inverse operation on the selected stored signal evolution.

More generally, the collection of stored signal evolutions include a signal selected from:

$$SE = \sum_{i=1}^{N_S} \prod_{i=1}^{N_A} \sum_{j=1}^{N_{RF}} R_{i(\alpha)} R_{RF_{ij}(\alpha,\phi)} R(G) E_i(T1, T2, \ldots) DPdM_0$$

or $$SE = \sum_{i=1}^{N_S} \prod_{i=1}^{N_A} \prod_{j=1}^{N_{RF}} R_i(\alpha) R_{RF_{ij}(\alpha,\phi)} R(G) E_i(T1, T2, \ldots) DPdM_0$$

where:

SE is a signal evolution, $N_S$ is a number of spins. $N_A$ is a number of sequence blocks, $N_{RF}$ is a number of RF pulses in a sequence block, $\alpha$ is a flip angle, $\phi$ is a phase angle, $Ri(\alpha)$ is a rotation due to off resonance, $R_{RF_{ij}}(\alpha, \phi)$ is a rotation due to RF differences, $R(G)$ is a rotation due to a gradient, T1 is spin-lattice relaxation, T2 is spin-spin relaxation, D is diffusion relaxation, Pd is proton density, $E_i(T1, T2, \ldots)$ is decay due to relaxation differences, and $M_0$ is the default or equilibrium magnetization.

In one embodiment, the collection of stored signal evolutions include a signal selected from:

$$S_i = R_i E_i (S_{i-1})$$

or $$S_i = R_i E_i \sum_{x=1}^{i-1} R_x E_x (S_x)$$

or $$S_i = R_i E_i \prod_{x=1}^{i-1} R_x E_x (S_x)$$

or $$S_i = \sum_{s=1}^{N_s} R_{s,i} E_{s,i} (S_{s,i-1})$$

or $$S_i = \sum_{s=1}^{N_s} R_{s,i} E_{s,i} \sum_{x=1}^{i-1} R_{s,x} E_{s,x} (S_{s,x})$$

or $$S_i = \sum_{s=1}^{N_s} R_{s,i} E_{s,i} \prod_{x=1}^{i-1} R_{s,x} E_{s,x} (S_{s,x})$$

where:

$S_0$ is the default or equilibrium magnetization, $S_i$ is a vector that represents the different components of the magnetization Mx, My, Mz during acquisition block i, $R_i$ is the combination of rotational effects that occur during acquisition block i, and $E_i$ is the combination of effects that alter the amount of magnetization in the different states for acquisition block i.

Apparatus 600 also includes a fraction logic 640 that identifies the relative proportions of the resonant species in the object. Identifying the relative proportions may be performed in different ways. In one example, the relative proportions may be decoded from the selected stored signal evolution. In another example, the relative proportions may be retrieved from a database, table, data store, or other location, process, or server using the selected stored signal evolution as reference information (e.g., a key).

Figure 7:
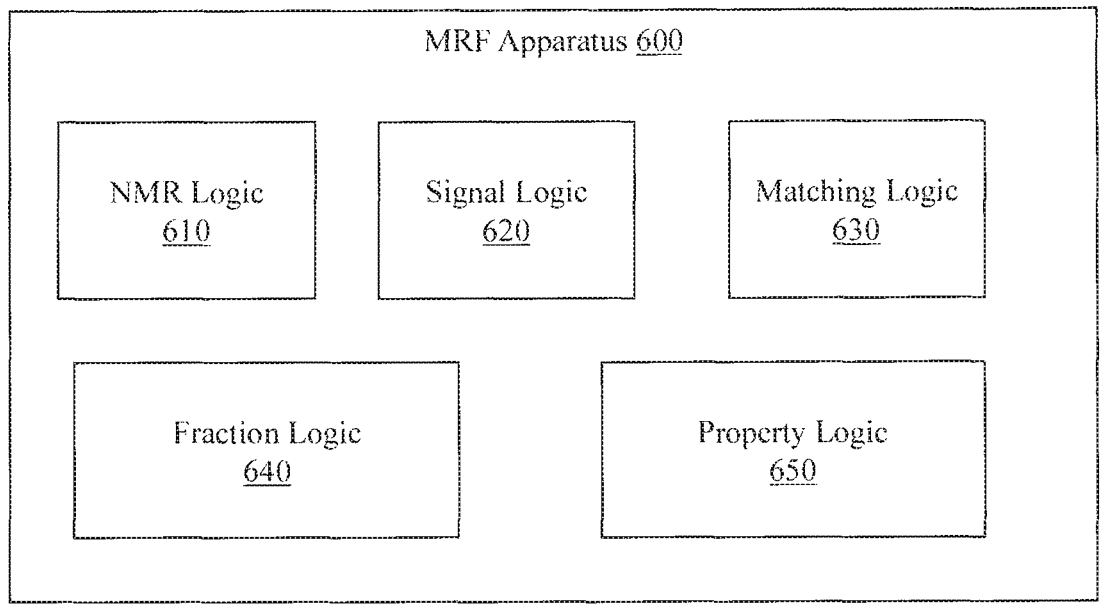
FIG. 7 illustrates an example MR apparatus associated with distinguishing healthy tissue from diseased tissue based on tissue component fractions identified using MRF.

FIG. 7 illustrates another embodiment of apparatus 600. This embodiment also includes a property logic 650. Property logic 650 identifies the object as having a property based, at least in part, on the relative proportions. The property may describe, for example, whether the object is diseased or healthy, whether the object is exhibiting indicia of multiple sclerosis, or other properties. In one embodiment, property logic 650 may determine whether a human brain includes fluid, cells, water interacting with cellular membranes in the human brain, and myelin water in proportions that indicate that the brain is affected by MS. Property logic 650 may determine whether other objects (e.g., liver, kidney) are affected by other conditions (e.g., cirrhosis, cancer).

While property logic 650 is illustrated as being part of MRF apparatus 600, in one embodiment, the property logic 650 may reside in an apparatus separate from the MRF apparatus 600. In this embodiment, MRF apparatus 600 may provide fraction data to the separate apparatus housing property logic 650.

Figure 8:
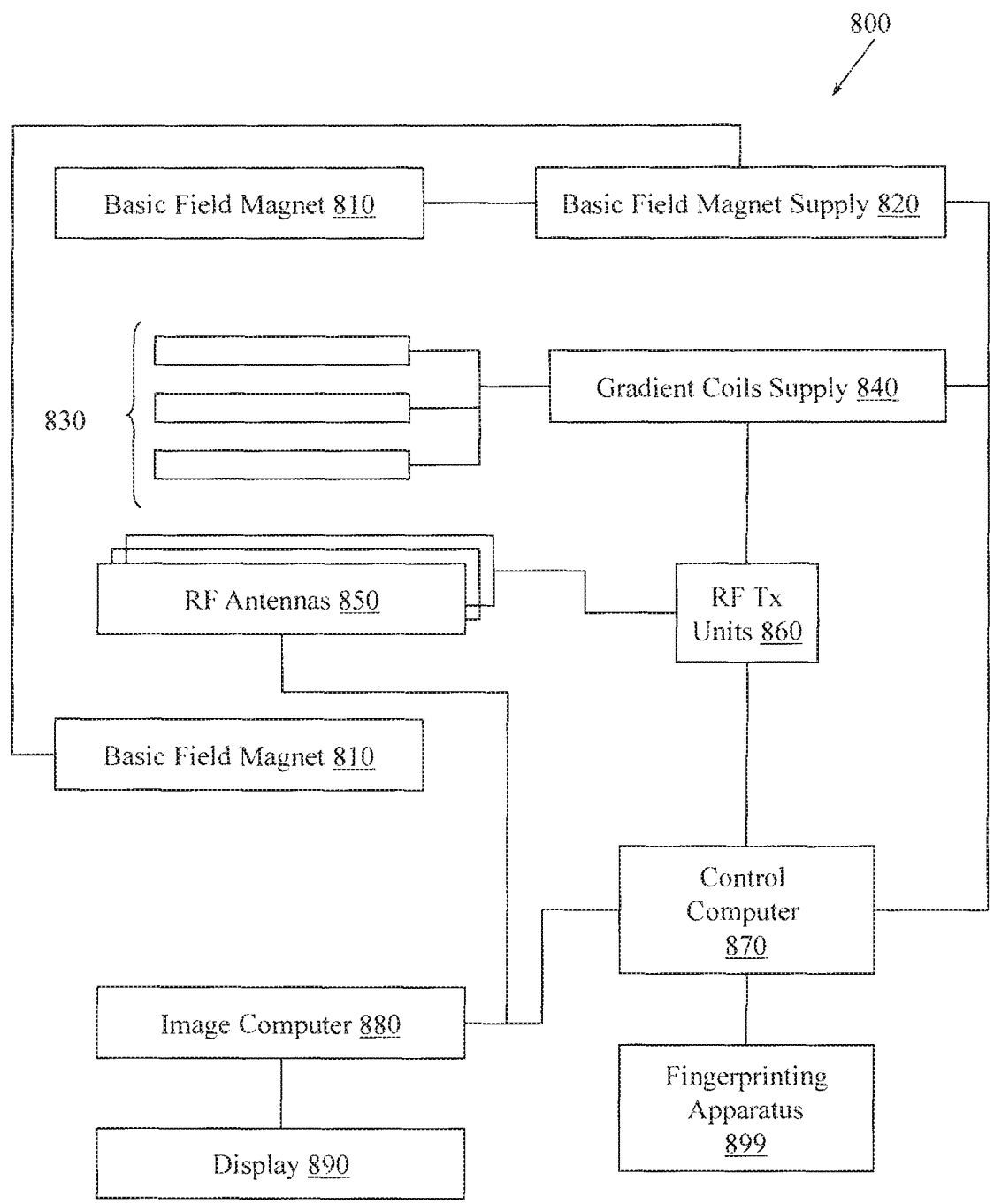
FIG. 8 illustrates an example MR apparatus associated with distinguishing healthy tissue from diseased tissue based on tissue component fractions identified using MRF.

FIG. 8 illustrates an example MR apparatus 800 having a fingerprinting apparatus 899 that facilitates MRF associated with distinguishing healthy tissue from diseased tissue. The distinguishing may be based, at least in part, on tissue component fractions. The fingerprinting apparatus 899 may be configured with elements of example apparatus described herein or may perform example methods described herein. While fingerprinting apparatus 899 is illustrated as part of MR apparatus 800, in one example, fingerprinting apparatus 899 may be a separate apparatus or apparatuses.

In one embodiment, fingerprinting apparatus 899 may include a collection logic that collects a received signal evolution from a tissue experiencing NMR in response to an MRF excitation applied to the tissue by the MRI apparatus 800. Fingerprinting apparatus 899 may also include a data store that stores a dictionary of MRF signal evolutions. Unlike conventional systems, members of the dictionary may be specially crafted combinations of constrained information associated with two or more resonant species. Information concerning the composition of the tissue with respect to the two or more resonant species is retrievable using a matched signal evolution. The fingerprinting apparatus 899 may also include a selection logic that selects a matching member of the dictionary that is most closely related to the signal evolution and establishes the matching member as the matched signal evolution. Fingerprinting apparatus 899 may also include a characterization logic that identifies a category for the tissue based, at least in part, on the composition of the tissue as identified using the matched signal evolution. The characterization logic may identify the category for the tissue using a quantitative magnetic resonance based approach. The category for the tissue may distinguish healthy tissue from diseased tissue.

The apparatus 800 includes a basic field magnet(s) 810 and a basic field magnet supply 820. Ideally, the basic field magnets 810 would produce a uniform B0 field. However, in practice, the B0 field may not be uniform, and may vary over an object being analyzed by the MR apparatus 800. MR apparatus 800 may include gradient coils 830 that emit gradient magnetic fields like $G_S$, $G_P$ and $G_R$. The gradient coils 830 may be controlled, at least in part, by a gradient coils supply 840. In some examples, the timing, strength, and orientation of the gradient magnetic fields may be controlled, and thus selectively adapted, during an MR procedure.

MR apparatus 800 may include a set of RF antennas 850 that generate RF pulses and receive resulting NMR signals from an object to which the RF pulses are directed. In some examples, how the pulses are generated and how the resulting MR signals are received may be controlled and thus may be selectively adapted during an MR procedure. Separate RE transmission and reception coils can be employed. The RF antennas 850 may be controlled, at least in part, by a set of RE transmission units 860. An RF transmission unit 860 may provide a signal to an RF antenna 850.

The gradient coils supply 840 and the RF transmission units 860 may be controlled, at least in part, by a control computer 870. In one example, the control computer 870 may be programmed to control an NMR device as described herein. Conventionally, the MR signals received from the RF antennas 850 can be employed to generate an image and thus may be subject to a transformation process like a two dimensional FFT that generates pixilated image data. The transformation can be performed by an image computer 880 or other similar processing device. The image data may then be shown on a display 890.

Fingerprinting apparatus 899 facilitates not having to do conventional reconstruction of an image from MR signals received from the RF antennas 850. Thus the RE energy applied to an object by apparatus 800 need not be constrained to produce signals with substantially constant amplitudes or phases. Instead, fingerprinting apparatus 899 facilitates matching received signals to known signals for which a reconstruction, relaxation parameter, or other information is already available.

While FIG. 8 illustrates an example MR apparatus 800 that includes various components connected in various ways, it is to be appreciated that other MR apparatus may include other components connected in other ways.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, determining, and so on, refer to actions and processes of a computer system, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 9:
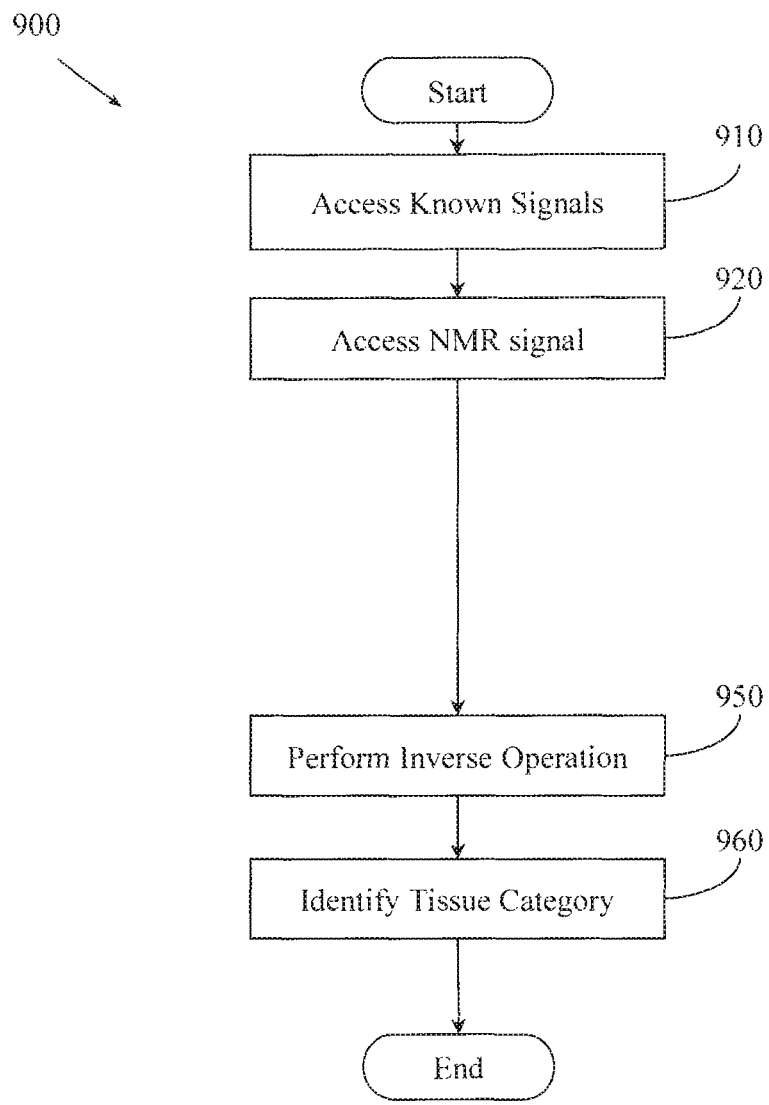
FIG. 9 illustrates an example method associated with distinguishing healthy tissue from diseased tissue based on tissue component fractions identified using MRF.

FIG. 9 illustrates a method 900 associated with distinguishing diseased tissue from healthy tissue based on tissue component fractions using MRF. Method 900 includes, at 910, accessing a set of known MRF signal evolutions. Unlike conventional systems, a member of the set of known MRF signal evolutions may have been produced by combining constrained data associated with NMR signals associated with a plurality of selected resonant species. In one embodiment, combining the data involves using a forward operation (e.g., weighted sum) for which an inverse operation (e.g., matrix pseudo-inverse) that identifies relative fractions of resonant species associated with the member is available.

Method 900 also includes, at 920, accessing an acquired NMR signal. The acquired NMR signal was produced by a volume that may contain different resonant species in different proportions. For example, the volume may be a brain and the resonant species may include fluid, cells, water interacting with cellular membranes, myelin water and other resonant species found in the brain. The different resonant species simultaneously produce individual NMR signals in response to MRF excitation produced by an MRF pulse sequence.

Method 900 also includes, at 950, performing the inverse operation on the acquired NMR signal to determine relative fractions of the resonant species in the volume. In one embodiment, the relative fractions concern normal white matter, normal appearing but abnormal white matter associated with multiple sclerosis, normal grey matter, normal appearing but abnormal grey matter associated with multiple sclerosis, or a lesion associated with multiple sclerosis. Other relative fractions may be considered. Understanding which resonant species are present and in which proportion to each other may facilitate making a diagnosis. For example, healthy tissue may include fluid, cells, water interacting with cellular membranes, and myelin water in first proportions to each other while diseased tissue may include fluid, cells, water interacting with cellular membranes, and myelin water in second proportions to each other. For example, in brain tissue affected by MS the amount of myelin water may be lower than in healthy tissue with respect to fluid and cells.

In one embodiment, method 900 also includes, at 960, identifying the volume as containing tissue that is a member of a tissue category. The tissue category may be selected based, at least in part, on the relative fractions of the resonant species in the volume. In one embodiment, the tissue category may identify whether the tissue is exhibiting indicia of multiple sclerosis or is not exhibiting indicia of multiple sclerosis.

The stored signals and information derived from reference signal evolutions may be associated with a potentially very large data space. The data space for signal evolutions can be partially described by:

$$SE = \sum_{i=1}^{N_S} \prod_{i=1}^{N_A} \sum_{j=1}^{N_{RF}} R_{i(\alpha)} R_{RF_{ij}(\alpha,\phi)} R(G) E_i(T1, T2, \ldots) DP dM_0$$

where:

SE is a signal evolution, $N_S$ is a number of spins, $N_A$ is a number of sequence blocks, $N_{RF}$ is a number of RF pulses in a sequence block, a is a flip angle, φ is a phase angle, Ri(α) is a rotation due to off resonance, $R_{RF_{ij}}(\alpha, \phi))$ is a rotation due to RF differences, R(G) is a rotation due to a gradient, T1 is spin-lattice relaxation, T2 is spin-spin relaxation, D is diffusion relaxation, Pd is proton density, $E_i(T1, T2, \ldots)$ is associated with magnetization changes, and $M_0$ is the default or equilibrium magnetization.

Additionally or alternatively, the summation on j could be replaced by a product on j, e.g.:

$$SE = \sum_{i=1}^{N_S} \prod_{i=1}^{N_A} \prod_{j=1}^{N_{RF}} R_i(\alpha) R_{RF_{ij}(\alpha,\phi)} R(G) E_i(T1, T2, \ldots) DP dM_0$$

In one embodiment, the dictionary may store signals described by:

$$S_i = R_i E_i(S_{i-1}),$$

where:

$S_0$ is the default or equilibrium magnetization, $S_i$ is a vector that represents the different components of magnetization Mx, My, Mz during acquisition block i, $R_i$ is a combination of rotational effects that occur during acquisition block i, and $E_i$ is a combination of effects that alter the amount of magnetization in the different states for acquisition block i. In this embodiment, the signal at acquisition block i is a function of the previous signal at acquisition block i–1.

Additionally or alternatively, the dictionary may store signals described by:

$$S_i = R_i E_i \sum_{x=1}^{i-1} R_x E_x(S_x)$$

or $$S_i = R_i E_i \prod_{x=1}^{i-1} R_x E_x(S_x).$$

In this embodiment, the signal is a function of the current relaxation and rotation effects and of previous acquisitions. Additionally or alternatively, the dictionary may store signals described by:

$$S_i = \sum_{s=1}^{N_s} R_{s,i} E_{s,i}(S_{s,i-1}).$$

In this embodiment, voxels have multiple resonant species or spins, and the effects may be different for every spin within a voxel. Additionally or alternatively, the dictionary may store signals described by:

$$S_i = \sum_{s=1}^{N_s} R_{s,i} E_{s,i} \sum_{x=1}^{i-1} R_{s,x} E_{s,x}(S_{s,x})$$

or $$S_i = \sum_{s=1}^{N_s} R_{s,i} E_{s,i} \prod_{x=1}^{i-1} R_{s,x} E_{s,x}(S_{s,x})$$

In this embodiment, voxels may have multiple resonant species or spins, and the effects may be different for spins within a voxel, and thus the signal may be a function of the effects and the previous acquisition blocks. However, the set of known signal evolutions may include specially crafted signal evolutions as described herein.

While FIG. 9 illustrates various actions occurring in serial, it is to be appreciated that various actions illustrated in FIG. 9 could occur substantially in parallel. By way of illustration, a first process could control accessing known signals, a second process could control acquiring NMR signals and a third process could identify the volume as containing tissue that is a member of a tissue category. While three processes are described, it is to be appreciated that a greater and/or lesser number of processes could be employed.

Figure 10:
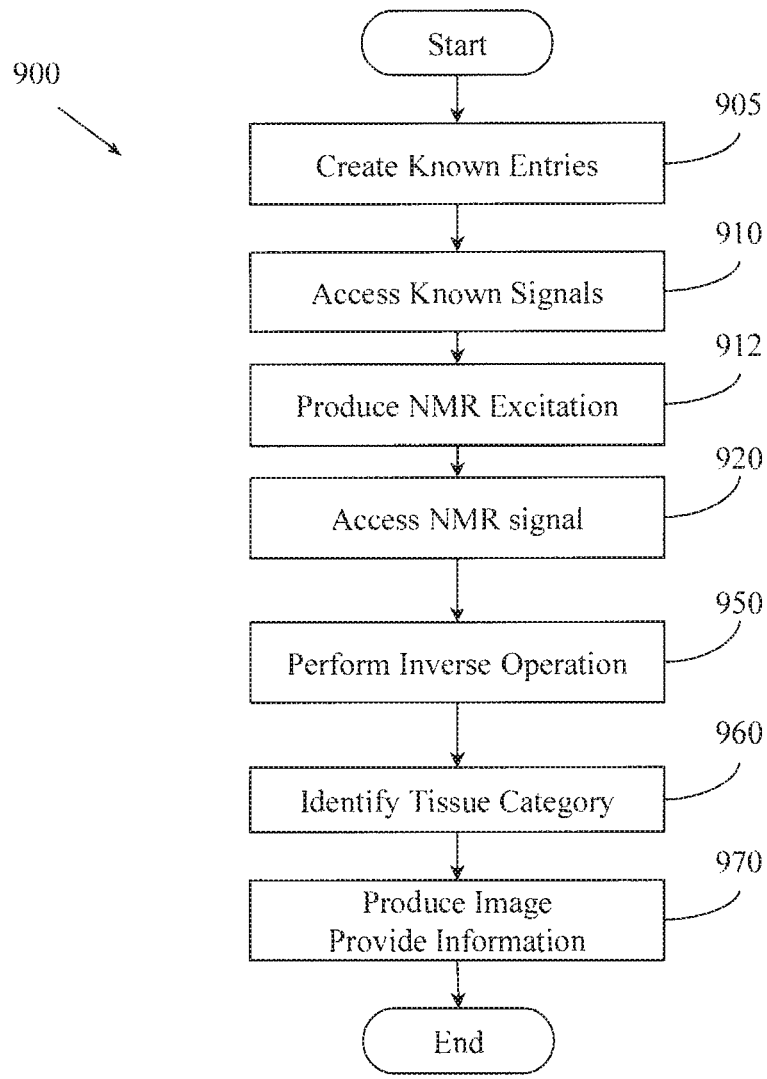
FIG. 10 illustrates an example method associated with distinguishing healthy tissue from diseased tissue based on tissue component fractions identified using MRF.

FIG. 10 illustrates another embodiment of method 900 (FIG. 9). This embodiment includes actions 910, 920, 950, and 960. However, this embodiment also includes actions 905, 912, and 970.

Action 905 includes creating the collection of stored entries or producing the set of known MRF signal evolutions. Producing the set of known MRF signal evolutions may include combining data associated with NMR signals associated with two or more resonant species using a weighted sum operation. In this embodiment, the inverse operation may be a matrix pseudo-inverse operation.

In one embodiment, producing the set of known MRF signal evolutions at 905 includes producing data associated with NMR signals by constraining first and second MR parameters associated with different resonant species. In one embodiment, producing the data includes varying a first MR parameter associated with a first resonant species contributing to the NMR signals while holding constant a second MR parameter associated with a second resonant species contributing to the NMR signals. In one embodiment, holding a parameter constant may include allowing the parameter to vary within a tight range (e.g., 1%, 5%) around a central value. The parameters may include T1 and T2. The first resonant species may include, for example, fluids found in a human brain, cells found in a human brain, and water interacting with cellular membranes. The second resonant species may include, for example, myelin water.

In one embodiment, producing the set of known MRF signal evolutions may include producing data associated with models of signal evolutions by holding T1 and T2 constant for a first resonant species, holding T1 and T2 constant for a second resonant species, holding T2 constant for a third resonant species, and varying T1 for the third resonant species. In one embodiment, T1 may be varied from 100 μs to 5000 ms for the third component. More generally, there may be X parameters for each of Y resonant species. All Y resonant species have the same X parameters. Producing the set of known MRF signal evolutions may include fixing one of the X parameters and sweeping through or varying other of the X parameters. In one embodiment, all the other X parameters may be varied while in another embodiment a subset of interesting X parameters may be varied.

Action 912 includes controlling the MRF apparatus to produce the MRF excitation using an MRF pulse sequence. Producing the MRF excitation is performed by applying RF energy to the volume in the object in a series of variable sequence blocks. Recall that an MRF sequence block includes one or more excitation phases, one or more readout phases, and one or more waiting phases. Recall also that at least one member of the series of variable sequence blocks differs from at least one other member of the series of variable sequence blocks in one or more sequence block parameters.

In one embodiment, action 912 includes controlling the NMR apparatus to vary a flip angle associated with the MRF pulse sequence or to vary the acquisition period in the MRF pulse sequence. Action 912 may also include varying other sequence block parameters including, but not limited to, echo time, phase encoding, diffusion encoding, flow encoding, RE pulse amplitude, RF pulse phase, number of RF pulses, type of gradient applied between an excitation portion of a sequence block and a readout portion of a sequence block, number of gradients applied between an excitation portion of a sequence block and a readout portion of a sequence block, an amount by which a gradient is unbalanced when applied between an excitation portion of a sequence block and a readout portion of a sequence bock, a type of gradient applied between a readout portion of a sequence block and an excitation portion of a sequence block, a number of gradients applied between a readout portion of a sequence block and an excitation portion of a sequence block, an amount by which a gradient is unbalanced when applied between a readout portion of a sequence block and an excitation portion of a sequence bock, a type of gradient applied during a readout portion of a sequence block, number of gradients applied during a readout portion of a sequence block, amount of RF spoiling, or an amount of gradient spoiling.

Action 912 may also include controlling the MRF apparatus to vary the amount of time between sequence blocks in the series of variable sequence blocks, the relative amplitude of RF pulses in sequence blocks in the series of variable sequence blocks, or the relative phase of RF pulses in sequence blocks in the series of variable sequence blocks.

This embodiment of method 900 also includes, at 970, producing an image. The image may be a T1 weighted image, a T2 weighted image, a proton density image map or other image. The image may be based, at least in part, on quantitative values associated with the selected entry. Instead of producing an image at 970, this embodiment may instead provide information about the object that was subjected to MRF. The information may include, for example, a diagnosis (e.g., MS, no-MS). In one embodiment, the information may concern the relative fractions or may concern the tissue category.

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, the invention is not limited to the specific details, the representative apparatus, and illustrative examples shown and described. Thus, this application is intended to embrace alterations, modifications, and variations that fall within the scope of the appended claims.

To the extent that the term "includes" or "including" is employed in the detailed description or the claims, it is inclusive in a manner similar to the term "comprising" as that term is interpreted when employed as a transitional word in a claim.

To the extent that the term "or" is employed in the detailed description or claims (e.g., A or B) it means "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one of, A, B, and C" is employed herein, (e.g., a data store configured to store one of, A, B, and C) it conveys the set of possibilities A, B, and C, (e.g., the data store may store only A, only B, or only C). It is not intended to require one of A, one of B, and one of C. When the applicants intend to indicate "at least one of A, at least one of B, and at least one of C", then the phrasing "at least one of A, at least one of B, and at least one of C" will be employed.

To the extent that the phrase "one or more of, A, B, and C" is employed herein, (e.g., a data store configured to store one or more of, A, B, and C) it conveys the set of possibilities A, B, C, AB, AC, BC, ABC, AA . . . A, BB . . . B, CC . . . C, AA . . . ABB . . . B, AA . . . ACC . . . C, BB . . . BCC . . . C, or AA . . . ABB . . . BCC . . . C (e.g., the data store may store only A, only B, only C, A&B, A&C, B&C, A&B&C, or other combinations thereof including multiple instances of A, B, or C). It is not intended to require one of A, one of B, and one of C. When the applicants intend to indicate "at least one of A, at least one of B, and at least one of C", then the phrasing "at least one of A, at least one of B, and at least one of C" will be employed.

What is claimed is:
1. An apparatus, comprising:
   a nuclear magnetic resonance (NMR) logic that receives a first set of data from a magnetic resonance fingerprinting (MRF) apparatus that repetitively and variably samples a (k, t, E) space associated with an object to acquire a set of NMR signals,
   where the MRF apparatus applies radio frequency (RF) energy to the object according to an MRF pulse sequence to cause the object to produce the set of NMR signals,
   where members of the first set of data are associated with different points in the (k, t, E) space, where t is time and E includes at least T1 and T2, T1 being spin-lattice relaxation and T2 being spin-spin relaxation, and where one or more of, t and E, vary non-linearly;
   a signal logic that produces an NMR signal evolution from the first set of data;
   a matching logic that selects, from a collection of stored signal evolutions, a selected stored signal evolution that matches the NMR signal evolution,
   where information concerning relative proportions of resonant species that contributed to the selected stored signal evolution is retrievable using the selected stored signal evolution.
2. The apparatus of claim 1, comprising:
   a characterization logic that retrieves the information concerning the relative proportions and identifies the object as having a property based, at least in part, on the relative proportions, where the property describes whether the object is diseased or healthy.

3. The apparatus of claim 2, where the property describes whether the object is exhibiting indicia of multiple sclerosis.

4. The apparatus of claim 2, where the collection of stored signal evolutions includes a signal evolution having information associated with a first resonant species and a second resonant species.

5. The apparatus of claim 4, where the information associated with the first resonant species is produced by controlling a magnetic resonance (MR) property associated with the first resonant species to be within a first known range and where the information associated with the second resonant species is produced by controlling the MR property associated with the second resonant species to be within a second known range.

6. The apparatus of claim 5, where the first resonant species is fluid found in a human brain, where the MR property for the fluid is T1, and where the first known range is between 2500 ms and 5000 ms.

7. The apparatus of claim 6, where the second resonant species is myelin water found in a human brain, where the MR property for the myelin water is T1, and where the second known range is between 100 μs and 1000 ms.

8. The apparatus of claim 7, where the information associated with the first resonant species is produced by controlling T2 associated with the first resonant species to be within 50 μs and 1000 ms and where the information associated with the second resonant species is produced by controlling T2 associated with the second resonant species to be within 15 ms and 25 ms.

9. The apparatus of claim 5, where the first resonant species is water interacting with cellular membranes found in a human brain, where the MR property for the cells is T1, and where the first known range is between 1000 ms and 1500 ms.

10. The apparatus of claim 9, where the second resonant species is myelin water found in a human brain, where the MR property for the myelin water is T1, and where the second known range is between 100 μs and 1000 ms.

11. The apparatus of claim 10, where the information associated with the first resonant species is produced by controlling T2 associated with the first resonant species to be within 50 μs and 1000 ms and where the information associated with the second resonant species is produced by controlling T2 associated with the second resonant species to be within 15 ms and 25 ms.

12. The apparatus of claim 1, where the collection of stored signal evolutions includes a signal evolution having information associated with fluid found in a human brain, cells found in a human brain, water interacting with a cellular membrane in the human brain, and myelin water found in a human brain, where the information associated with the fluid is produced by controlling T1 associated with the fluid to be between 4500 ms and 5000 ms and by controlling T2 associated with the fluid to be between 450 ms and 500 ms, where the information associated with the cells or water interacting with a cellular membrane in the human brain is produced by controlling T1 associated with the cells or water interacting with a cellular membrane in the human brain to be between 1000 ms and 1500 ms and by controlling T2 associated with the fluid to be between 100 ms and 150 ms, and where the information associated with the myelin water is produced by controlling T1 associated with the myelin water to be between 50 ms and 1000 ms and by controlling T2 associated with the fluid to be between 15 ms and 25 ms.

13. The apparatus of claim 5, where the information concerning the first resonant species is combined with the information concerning the second resonant species using a weighted sum operation.

14. The apparatus of claim 13, where the information concerning relative proportions of resonant species that contributed to the selected stored signal evolution is retrievable from the selected stored signal evolution in response to performing a matrix pseudo-inverse operation on the selected stored signal evolution.

15. The apparatus of claim 1, where the collection of stored signal evolutions include a signal selected from:

$$SE = \sum_{i=1}^{N_A} \prod_{i=1}^{N_A} \sum_{j=1}^{N_{RF}} R_{(\alpha)} R_{RFij(\alpha,\phi)} R(G) E_i(T1, T2, K) DPdM_0$$

or $$SE = \sum_{i=1}^{N_A} \prod_{i=1}^{N_A} \prod_{i=1}^{N_{RF}} R_{(\alpha)} R_{RFij(\alpha,\phi)} R(G) E_i(T1, T2, K) DPdM_0$$

where:
SE is a signal evolution,
$N_S$ is a number of spins,
$N_A$ is a number of sequence blocks,
$N_{RF}$ is a number of RF pulses in a sequence block,
α is a flip angle,
φ is a phase angle,
Ri(α) is a rotation due to off resonance,
$R_{RFij}(\alpha,\phi)$ is a rotation due to RF differences,
R(G) is a rotation due to a gradient,
T1 is spin-lattice relaxation,
T2 is spin-spin relaxation,
D is diffusion relaxation,
Pd is proton density,
$E_i(T1, T2, \ldots)$ is decay due to relaxation differences, and
$M_0$ is the default or equilibrium magnetization.

16. The apparatus of claim 1, where the collection of stored signal evolutions include a signal selected from:

$$S_i = R_i E_i(S_{i-1})$$

or $$S_i = R_i E_i \sum_{x=1}^{i-1} R_x E_x(S_x)$$

or $$S_i = R_i E_i \prod_{x=1}^{i-1} R_x E_x(S_x)$$

or $$S_i = \sum_{s=1}^{N_s} R_{s,i} E_{s,i}(S_{s,i-1})$$

or $$S_i = \sum_{s=1}^{N_s} R_{s,i} E_{s,i} \sum_{x=1}^{i-1} R_{s,x} E_{s,x}(S_{s,x})$$

or $$S_i = \sum_{s=1}^{N_s} R_{s,i} E_{s,i} \prod_{x=1}^{i-1} R_{s,x} E_{s,x} (S_{s,x})$$  (5)

where:
$S_0$ is the default or equilibrium magnetization,
$S_i$ is a vector that represents the different components of the magnetization Mx, My, Mz during acquisition block i,
$R_i$ is the combination of rotational effects that occur during acquisition block i, and
$E_i$ is the combination of effects that alter the amount of magnetization in the different states for acquisition block i.

17. A magnetic resonance imaging (MRI) apparatus, comprising:
- a collection logic that collects a received signal evolution from a tissue experiencing nuclear magnetic resonance (NMR) in response to a magnetic resonance fingerprinting (MRF) excitation applied to the tissue by the MRI apparatus;
- a data store that stores a dictionary of MRF signal evolutions, where members of the dictionary are combinations of information associated with two or more resonant species, and where information concerning the composition of the tissue with respect to the two or more resonant species is retrievable using a matched signal evolution;
- a selection logic that selects a matching member of the dictionary that is most closely related to the signal evolution and establishes the matching member as the matched signal evolution, and
- a characterization logic that identifies a category for the tissue based, at least in part, on the relative composition of the tissue as identified using the matched signal evolution.

18. The MRI apparatus of claim 17, where the characterization logic identifies the category for the tissue using a quantitative magnetic resonance based approach.

19. The MRI apparatus of claim 17, where the category for the tissue distinguishes healthy tissue from diseased tissue.

* * * * *